(12) United States Patent
Skabelund

(10) Patent No.: US 6,749,871 B2
(45) Date of Patent: Jun. 15, 2004

(54) COMPOSITIONS FOR TREATING SYMPTOMS OF UROGENITAL/UROLOGICAL DISORDERS

(75) Inventor: Robert E. Skabelund, Logan, UT (US)

(73) Assignee: Prater Herbs, L.L.C., Logan, UT (US)

( * ) Notice: Subject to any disclaimer, the term of this patent is extended or adjusted under 35 U.S.C. 154(b) by 0 days.

(21) Appl. No.: 10/141,492

(22) Filed: May 8, 2002

(65) Prior Publication Data

US 2003/0211174 A1 Nov. 13, 2003

(51) Int. Cl.⁷ .............................................. A61K 35/78
(52) U.S. Cl. ....................... 424/725; 424/764; 424/773; 424/777
(58) Field of Search ................................ 424/725, 764, 424/773, 776, 777

(56) References Cited

U.S. PATENT DOCUMENTS

| | | | |
|---|---|---|---|
| 4,198,401 A | 4/1980 | Pegel | 424/195 |
| 4,258,037 A | 3/1981 | Juvin | 424/195 |
| 5,273,747 A | 12/1993 | Bombardelli et al. | 424/195.1 |
| 5,543,146 A | 8/1996 | Perez | 424/195.1 |

OTHER PUBLICATIONS

Computer website: http://web.florahealth.com/flora/home/Canada/healthinformation/encyclopedias/DandelionLeaf.asp Date si Jul. 2001.*

Computer website: http://thefoodstores.com/thp/html/dherbs2.htm. Date of site2001.*

* cited by examiner

Primary Examiner—Herbert J. Lilling
(74) Attorney, Agent, or Firm—Stoel Rives LLP

(57) ABSTRACT

Compositions and methods are provided for aiding human beings to complete emptying of the bladder, to reduce urination frequency, to alleviate the urgency and difficulty in postponing urination, to lessen the interruption in urinating, to increase the urinary stream flow, to facilitate the beginning of urination, to reduce nocturia, or to increase libido. These advantages are achieved by administering to a human being a preparation with at least a part of at least one plant in family Asteraceae. Preparations from a part of the plant *Wyethia amplexicaulis* are preferred. Other examples of suitable plants include *Balsamorhiza sagittata, Helianthella uniflora*, and *Tragopogon dubius*. The treatment composition may include parts of the plants or an active agent obtained from one of these plants and isolated or a synthetic equivalent.

13 Claims, 2 Drawing Sheets

© 1995 Utah State University Press

© 1995 Utah State University Press

© 1995 Utah State University Press

© 1995 Utah State University Press

COMPOSITIONS FOR TREATING SYMPTOMS OF UROGENITAL/UROLOGICAL DISORDERS

THE FIELD OF THE INVENTION

The present invention relates to compositions for treating urogenital and urological disorders. The present invention relates in particular to compositions that are useful in treating symptoms of interstitial cystitis benign prostatic hypertrophy (BPH).

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

PRESENT STATE OF THE ART

The likelihood of experiencing urological difficulties increases for both men and women with aging. Approximately 2 million women in the United States suffer from interstitial cystitis, a painful condition with an unknown pathophysiology. The percentage of men that experience urological difficulties is pronounced primarily due to complications related to the prostrate gland.

The symptoms of interstitial cystitis and BPH vary, but the most common symptoms involve changes or problems with urination, such as a hesitant, interrupted, and/or weak stream; urgency and leaking or dribbling; and more frequent urination, especially at night (nocturial). Symptoms of interstitial cystitis also include discomfort or pain in the bladder or pelvic area and scarring or stiffness in the bladder wall. The American Urological Association (hereinafter "AUA") has developed a questionnaire to evaluate the symptoms of urological disorders as provided in detail in the section below entitled "Examples of the Invention." This questionnaire focuses on matters such as sensation of not completely emptying the bladder upon urination, urination frequency, intermittent urination, difficulty in postponing urination, weak urinary stream flow characteristics, and difficulty in urinating urgency for night time urination. The sum of the answers is the symptom score. For men, a urological disorder score from 1–7 is mild prostatism; a score from 8–19 is moderate prostatism; and a score from 20–35 is severe prostatism. For women, a urological disorder score from 1–7 is mild interstitial cystitis; a score from 8–19 is moderate interstitial cystitis; and a score from 20–35 is severe interstitial cystitis. See, for example, S. Margolis and H. Ballentine Carter, *Prostate Disorder*, at 13, The Johns Hopkins Medical Institutions (1997).

The causes of interstitial cystitis are currently not well understood. Theories to explain interstitial cystitis include the theory that interstitial cystitis is an autoimmune response following a bladder infection. Another theory is that interstitial cystitis is caused by a bacterial infection which is not detectable in urine tests. Because the cause of interstitial cystitis is unknown, treatment mainly focuses on reducing symptoms. Bladder distension, often done to diagnose IC, can reduce symptoms. A bladder instillation or bladder wash, in which the bladders is filled with a solution held for a period of 10 to 15 minutes, is another common interstitial cystitis treatment. The bladder instillation may also include the drug, dimethyl sulfoxide.

Treatment for interstitial cystitis may include drugs administered orally, and in severe cases, surgery. Drugs such as pentosan polysulfate sodium, antidepressants, and antihistamines have been used to treat interstitial cystitis. Surgical options include fulguration and resection of ulcers, bladder augmentation, and bladder removal. Fulguration is the burning of ulcers with a laser or with electricity. After the area heals, the dead tissue sloughs off, leaving new, healthy tissue. Resection of ulcers involve cutting around and removing ulcers.

Bladder augmentation involves removing damaged portions of the bladder. A portion of the patient's large intestine is then removed and attached to the bladder. After-effects of this surgery may include infection in the bladder and difficulty absorbing nutrients from the intestine. In addition, the symptoms of interstitial cystitis, pain, frequency and urgency, may continue even after surgery.

Another surgical option, bladder removal, requires urine to be rerouted. In a urostomy, a ureter is attached to a piece of bowel that opens onto the skin in the abdomen. Urine is emptied through the opening in the skin and into a bag, either outside the body or inside the abdomen. The area around the opening must be kept clean to avoid infection. Since surgical solutions for interstitial cystitis can have many adverse side effects, surgery is generally an option in only the most severe cases. An improved orally-administered treatment for interstitial cystitis is needed.

Like interstitial cystitis, causes for BPH are unknown. However, BPH may be caused by an enlarged prostate. It is common for the prostate gland to become enlarged as a man ages. As a male matures, the prostate goes through two main periods of growth. The first occurs early in puberty when the prostate doubles in size. At around age 25 the gland begins to grow again. It is this second growth phase that often results, years later, in the condition know as benign prostatic hyperplasia or benign prostatic hypertrophy (hereinafter "BPH"). Statistically, BPH rarely causes symptoms before age 40, but more than half of men in their sixties and as many as 90 percent in their seventies and eighties have some symptoms of BPH. As the prostate enlarges, the surrounding capsule stops it from expanding, causing the gland to press against the urethra. The bladder wall becomes thicker and irritable. The bladder begins to contract even when it contains small amounts of urine, causing more frequent urination. As the bladder weakens, it loses the ability to empty itself, and urine remains behind. This narrowing of the urethra and partial emptying of the bladder cause many of the problems associated with BPH.

Men who experience symptoms that cause major inconvenience or health risk usually need some kind of treatment. Most doctors recommend removal of the enlarged part of the prostate as the best long-range solution for patients with BPH. Surgery for BPH removes only the enlarged tissue that is pressing against the urethra. The rest of the prostate is left intact. A common surgery of this type is transurethral resection of the prostate (TURP). With the TURP procedure, an instrument called a resectoscope is inserted through the penis. The resectoscope, which is about 12 inches long and one-half inch in diameter, contains a light, valves for controlling irrigating fluid, and an electrical loop that cuts tissue and seals blood vessels. The pieces of cut tissue are carried by fluid into the bladder and then flushed out at the end of the operation.

Another surgical procedure is called transurethral incision of the prostate (TUIP). Instead of removing tissue, as with the TURP procedure, this procedure widens the urethra by making a few small cuts in the bladder neck and in the prostate gland itself. Other new treatment techniques are also being investigated, such a laser surgery, microwave thermotherapy and prostatic stents. Transurethral procedures are less traumatic than open forms of surgery and usually require a shorter recover period.

Reportedly, the management of benign prostatic hyperplasia is in transition. See, for example, J. E. Oesterling, *Benign Prostatic Hyperplasia, The New England Journal of Medicine* 99, Vol. 332(2) (1995). In addition to surgical treatment, non-surgical drug therapies are also being investigated, such as androgen-deprivation therapy and a-adrenergic antagonists. For example, the 5a-reductase inhibitor, Finasteride, in a three-year clinical evaluation showed reduction in prostatic volume by about 27%, improvement in urinary flow rate by 2.3 ml per second, and a reduction in symptom score by 3.6 points. However, about four to five percent of the participants experienced side effects such as decreased libido and impotence. See, J. E. Oesterling and J. M. Monda, *Contemporary Urology*, at 55, 58, Vol. 6(1) (1994).

Among physiotherapeutic agents, it is known that the use of saw palmetto and other plant-derived substances for BPH has been popular in Europe and other parts of the world, including the Untied States. These substances include the fruit and pollen of *Serenoa repens, Sabal serrulata* syn. *Serenoa serrulata* (Palmaceae), popularly known as saw palmetto. As reported by S. Margolis and H. Ballentine Carter in 1997 at page 23 in Prostate Disorders of The Johns Hopkins Medical Institutions, it "remains to be seen whether these agent are truly effective." They also stated at page 23 that "[v]arious studies have reported a 60% to 80% improvement in BPH symptoms from these agents, but most of this research was poorly designed and none reported any significant rise in urinary flow rate." They further stated at page 23 that until "well-designed clinical trials show a benefit over placebo, and compare them to treatments known to work, phytotherapeutic agents cannot be considered effective therapy for BPH."

Despite advances in the treatment of urogenital/urological disorders such as interstitial cystitis and BPH, there continues to be a need in the art for effective treatments for the symptoms associated with such disorders, particularly non-surgical treatments.

BRIEF SUMMARY OF THE INVENTION

It is an object of the present invention to provide a treatment of urogenital/urological disorders such as interstitial cystitis and BPH.

It is also an object of the present invention to provide a treatment of urogenital/urological disorders such as BPH without utilizing surgical treatments.

To achieve the foregoing objects, and in accordance with the invention as embodied and broadly described herein in the preferred embodiment, a process is provided for treating a human being to aid in the complete emptying of the bladder, to reduce urination frequency, to alleviate the urgency and difficulty in postponing urination, to lessen the interruption in urinating, to increase the urinary stream flow, to facilitate the beginning of urination, to reduce nocturia, or to increase libido. The invention involves administering to a human being a preparation that includes at least a part of at least one plant in family Asteraceae. Preparations from the plant *Wyethia amplexicaulis* are preferred. Other examples of suitable plants for use in treatment compositions include *Balsamorhiza sagittata, Helianthella uniflora*, and *Tragopogon dubius*. The composition or preparation is administered to a human being in an amount sufficient to reduce the Urological Disorder Symptom List score of the human being. The invention also involves preparing the composition from the plants. Additionally, an active agent may be obtained from one of these plants and an isolated or a synthetic equivalent may be manufactured that can be used to treat urological/urogenital disorders.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended photographs.

DETAILED DESCRIPTION OF THE PREFERRED EMBODIMENTS

The present invention is directed to an herbal composition useful in treating symptoms of urogenital and urological disorders such as interstitial cystitis and benign prostatic hypertrophy (BPH). The herbal compositions within the scope of the present invention include one or more ingredients taken from a plant in the family Asteraceae. Particularly preferred are compositions including one or more ingredients taken from the plant *Wyethia amplexicaulis*, commonly known as wyethia, mule ear or mule ear dock. Other examples of plants in the family Asteraceae that may be used in an herbal compositions include: arrowleaf balsamroot (*Balsamorhiza sagittata*); little sunflower (*Helianthella uniflora*); and salsify (*Tragopogon dubius*).

The plants can be used individually or in combination to produce beneficial activity. Mule ear dock provides particularly good results. All parts of the plants, including the stem, leaves, flowers, and seeds, can be included in the compositions within the scope of the present invention. The leaves and stems are preferred because they are easily harvested and processed. In addition to arrowleaf balsamroot, little sunflower, mule ear dock, and salsify, their hybrids may also be utilized.

Additionally, one or more active agents may be obtained from one or more of these plants and isolated and included in a composition in a concentration that is sufficient to achieve a therapeutic effect. It is also possible to synthetically from an active agent that substantially corresponds with the isolated active agent(s) obtained from the plants that achieves essentially the same therapeutic effect.

Figure 1:
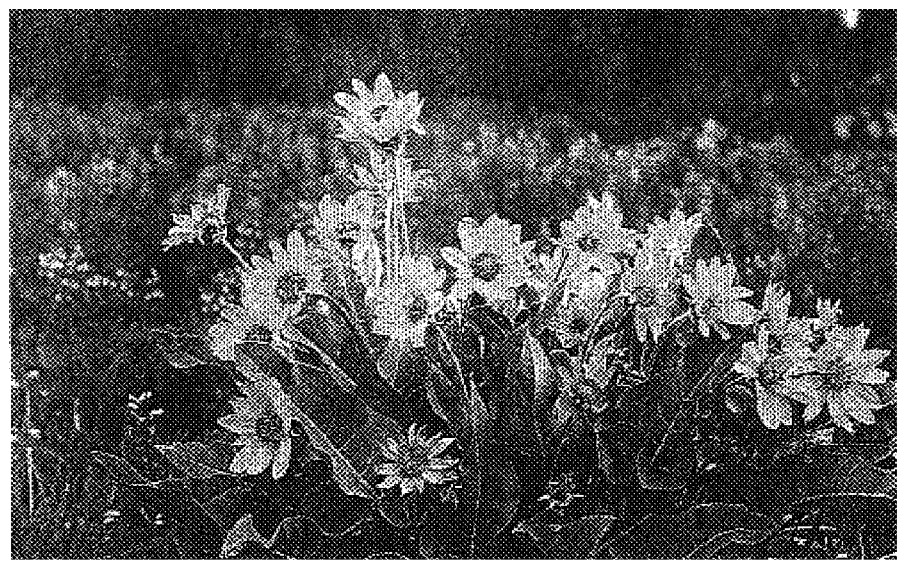
FIGS. 1 and 2 are photographs of specimens of arrowleaf balsamroot.
Figure 2:
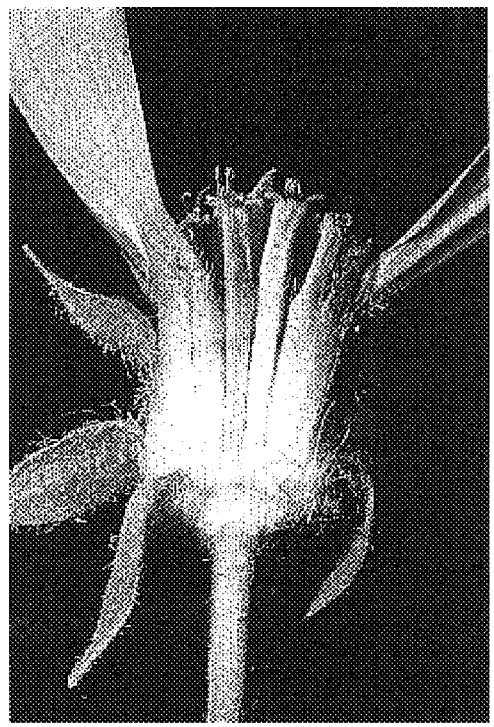
Figure 3:
FIG. 3 is a photograph of a specimen of little sunflower.

FIGS. 1 and 2 are photographs of specimens of an arrowleaf balsamroot plant. Arrowleaf balsamroot is a perennial plant that typically grows 1 foot to 2 feet tall. It blooms in a large yellow sunflower-like flower that is mostly solitary at the end of the stem. Its leaves are arrowhead shaped, grey-green, white-woolly, long stalked and basal. The stems are erect, ascending and woolly. Arrowleaf balsamroot has a deep-set taproot with pleasant balsam odor, and it propagates by seed dispersion. It preferably grows at elevations within the range of approximately 4500 feet to 7000 feet, with a moisture requirement of 10 inches to 18 inches. It is found on foothills and lower mountains growing on soil that ranges from soil having a relatively high gravel content to soil that is relatively clayish; with range sites in mountain, upland and semi-desert clay to gravelly loam FIG. 3 provides a photograph of a specimen of a little sunflower. Little sunflower is a perennial plant. It blooms in a large yellow sunflower-like flower. Its stems are clustered from a branching caudex and are typically 2–10 dm tall. Its leaves are simple and are typically opposite but occasionally alternate. Little sunflower has a stout taproot. It typically grows in hillsides and open woods.

Figure 4:
FIG. 4 is a photograph of a specimen of mule ear.

FIG. 4 provides a photograph of a specimen of mule ear. Mule ear is a perennial native plant that is typically 1 foot to 2 feet tall. Its flowers are large, yellow, sunflower-like and solitary on the stem. Its leaves are dark green, glossy, lance-shaped, like the ears of a mule. The stems are stout and erect and the plant has a thick woody taproot. Typically, this plant gives off odor in June and it propagates by seeds. It usually grows at elevations within the approximate range of 4500 feet to 9000 feet in moist valleys and mountain slopes. The moisture requirement is between 10 inches and 18 inches. It is found in soil that ranges from soil having a relatively high gravel content to soil that is relatively clayish; with range sites in high mountain and upland stony loam, growing on mountain clay or gravelly loam.

Salsify (not shown) is a biennial or annual introduced plant that typically grows 1 foot to 3 feet tall. Its flower heads are lemon-yellow with long pointed sepals or bracts under the petals; in late summer a seed head forms a ball of white fluff. Leaves are long grass-like clasping the erect stem. Salsify typically propagates by wind dispersed seed, and it preferably grows at an elevation in the range of approximately 4000 feet to approximately 5100 feet. its moisture requirement is 14 inches to 25 inches. It is found on valleys and foothills on moist loamy or sandy soil; with range sites in upland shallow loams.

The plants are preferably harvested when full-grown and still green. After the plants are picked they are cleaned. For example, the plants may be washed in clear water and then rinsed in a disinfecting solution. This solution preferably comprises three tablespoons of household bleach to five gallons of water. The plants or parts of the plants are subsequently dried. They may be mechanically pulverized and placed in capsules that consequently contain the plants' components. These capsules are preferably 500 mg capsules.

In addition to pulverized plants in capsules, the plants may be delivered in other compositions. For example, the plants, particularly the plant leaves, may be used prepare an herbal tea which contains active plant components and produces the desired beneficial activity. While the plants may be packaged for mixing with a liquid to be ingested as an herbal tea, the plants are preferably packaged in the capsule because of the greater ability to control dosage.

The capsules are preferably administered ingested once a day in the morning. Up to two capsules a day can be administered. An optimum dosage can be determined through routine experimentation.

EXAMPLES OF THE INVENTION

The following Examples are given to illustrate the present invention, and are not intended to limit the scope of the invention. The Examples report results of tests performed on a sample of human individuals and the assessment of the evolution of each individual. More particularly, the condition of each individual was assessed through the use of the questionnaire entitled Urological Disorder Symptom Checklist provided by the American Urological Association ("Symptom Checklist") and was then reassessed throughout the treatment using the same questionnaire. As referenced above in the section of the application entitled "Background of the Invention", the questionnaire focuses on matters such as sensation of not completely emptying the bladder upon urination, urination frequency, intermittent urination, difficulty in postponing urination, weak urinary stream flow characteristics, and difficulty in urinating urgency for night time urination. The sum of the answers is the symptom score. A Symptom score from 1–7 is mild prostatism; a score from 8–19 is moderate prostatism; and a score from 20–35 is severe prostatism. Generally, no treatment is needed if symptoms are mild; moderate symptoms are considered as requiring some form of treatment; and severe symptoms are conventionally considered as indicating that surgery is necessary. Reproduced in Table A below is an example of the questionnaire used in the studies of individuals provided below as Examples 1–9.

TABLE A

|  | Not at all | Less than 1 time in 5 | Less than half the time | About half the time | More than half the time | Almost always |
|---|---|---|---|---|---|---|
| 1. Over the past month, how often have you had a sensation of not emptying your bladder completely after you finished urinating? | 0 | 1 | 2 | 3 | 4 | 5 |
| 2. Over the past month, how often have you had to urinate again less than two hours after you finished urinating? | 0 | 1 | 2 | 3 | 4 | 5 |
| 3. Over the past month, how often have you found you stopped and started again several time when you urinated? | 0 | 1 | 2 | 3 | 4 | 5 |
| 4. Over the past month, how often have you found it difficult to postpone urination? | 0 | 1 | 2 | 3 | 4 | 5 |
| 5. Over the past month, how often have you had a weak urinary stream? | 0 | 1 | 2 | 3 | 4 | 5 |

TABLE A-continued

|  | Not at all | Less than 1 time in 5 | Less than half the time | About half the time | More than half the time | Almost always |
|---|---|---|---|---|---|---|
| 6. Over the past month, how often have you had to push or strain to begin urination? | 0 | 1 | 2 | 3 | 4 | 5 |
| 7. Over the past month, how many times did you most typically get up to urinate from the time you went to bed at night until the time you got up in the morning? | 0 | 1 | 2 | 3 | 4 | 5 |

Several individuals, ranging in age from 52 to 85, participated in the studies to assess the efficacy of the herbal compositions within the scope of the present invention. Before becoming a participant in the study group, each participant completed the questionnaire shown in Table A and underwent a battery of blood tests which included a Chemistry Panel with differential, and a Liver Panel. Male participants also underwent a blood test for Prostate Specific Antigen. These tests were performed to establish a baseline on the patients overall health before the studies with compositions within the scope of the present invention began. The tests were required monthly thereafter to track the effects of the herbal treatment. Additionally, each participant was required to complete a Medical History Questionnaire which inquired for age, height, weight, history of prostate disease, prostate cancer, or bladder or urinary tract problems, other medical problems, and any medication being taken.

Each participant was required to complete initially and monthly thereafter, the Symptom Checklist which is a questionnaire developed to evaluate the severity of urological disorder symptoms in both men and women. Each month the participants were required to document daily, on a calendar provided to them, any changes in their symptoms as they were experienced.

Example 1

A male, age 73, weight 143 lbs, had a beginning Symptom Checklist score of 9. After about two months of treatment with a daily dosage of the 500 mg herbal composition described hereinabove, his Symptom Checklist score decreased to a value of 5.

He had been diagnosed with prostate cancer in 1972 and subsequently had his prostate removed. His symptoms were nocturia and incontinence. This individual was incorporated in the study group precisely because his prostate has been removed. Consequently, the evolution of this subject's symptoms would be that of a male subject whose bladder and urinary symptoms were not being caused by an enlarged prostate. Prior to treatment with the herbal compositions according to this invention, he was getting up four times a night to urinate. After an approximately two-month treatment period, this individual expressed that he felt that his incontinence has decreased in severity and that he felt better all around.

Example 2

A female, age 81, weight 130 lbs, had a beginning Symptom Checklist score of 27. After about three months of treatment with the 500 mg herbal composition described hereinabove, her Symptom Checklist score decreased to a value of 9.

She began the study suffering from severe urinary incontinence. She was scoring at the highest score possible for not being able to empty her bladder, being unable to postpone urination, and having a weak urinary stream. Over the course of the treatment with the herbal compositions according to this invention she experienced a vast improvement in those three categories plus a good improvement in the other four categories in the Symptom Checklist. This individual was a female and suffering from urinary problems not related to prostate disease, yet the improvement in her symptoms was as pronounced as the improvement generally observed in the male participants with prostate disease.

Example 3

A male, age 83, weight 155 lbs, had a beginning Symptom Checklist score of 4. After about three months of treatment with the 500 mg herbal composition described above, his Symptom Checklist score had decreased to 0.

Over the course of treatment the participant's urinary stream became stronger and more spontaneous. He was gradually and increasingly able to more easily postpone urination and experienced a gradual reduction in the amount of straining to urinate. He had been experiencing only mild symptoms at the beginning of the study. All of his symptoms improved and he reported to be symptom free at the end of the study.

Example 4

A male, age 52, weight 204 lbs, had a beginning Symptom Checklist score of 6. After about two months of treatment with the 500 mg herbal composition described hereinabove, his Symptom Checklist score had decreased to a value of 5.

This participant's most prevalent symptoms at the beginning of testing were nocturia and a weak urinary stream. Although the improvement in the nocturia symptoms were marginal, the strength of the urinary stream improved. he also reported increased libido since the beginning of the study, a positive side affect that was not expected.

Example 5

A male, age 55, weight 168 lbs, had a beginning Symptom Checklist score of 14. After about two months of treatment with the 500 mg herbal composition described hereinabove, his Symptom Checklist was 14.

This participant did not experience an observed significant improvement as reflected in the Symptom Checklist. Some of his scores actually increased slightly. Nevertheless, he experienced improvement in his nocturia. His condition evolved from one in which he used to awake twice a night to an improved condition of not awakening at all to urinate during the night.

Example 6

A male, age 77, weight 174 lbs, had beginning BPH Symptom Checklist score of 20. After about two months of treatment with the 500 mg herbal composition described hereinabove, his Symptom Checklist score had decreased to a value of 10.

This participant' chief symptoms at the beginning of testing were frequent urination both day and night and pain associated with an enlarged prostate. He experienced a marked improvement in being able to completely empty his bladder, his urinary stream increased in strength, and the number of times he urinated at night was reduced from three times a night to about once a night. This individual also reported that the pain and discomfort associated with his enlarged prostate had markedly diminished.

Example 7

A male, age 85, weight 163 lbs, had a beginning Symptom Checklist score of 20. After about four months of treatment with the 500 mg herbal composition described hereinabove, his Symptom Checklist score had decreased to a value of 5.

This participant was scoring high in six out of seven categories in the Symptom Checklist. He was symptomatic for every symptom except urinary stream. After four months he improved remarkably in five out of the six categories. He improved emptying of his bladder, his ability to postpone urination for longer periods of time improved, his urinary stream was reported as having become stronger he did not have to keep pushing or straining to urinate, and instead of waking four times a night to urinate he awoke only twice after the four month treatment.

Example 8

A male, age 67, weight 195 lbs, had a beginning Symptom Checklist score of 12. After about one month of treatment with the 500 mg herbal composition described hereinabove, his Symptom Checklist score had decreased to a value of 4.

This participant's symptoms were nocturia and impotency. He reported trying many over-the-counter remedies with no success. Prior to the treatment, he got up three to four times a night to urinate. This frequency was reduced to once with the treatment for about one month with the compositions according to this invention. This individual reported at the end of the approximately one-month treatment that he felt better and satisfied with the improvement that he had experienced, especially regarding the change in the PSA test results that decreased from a 8.7 to 7.1.

Example 9

A male, age 62, weight 185 lbs, had a beginning Symptom Checklist score of 23. After about two months of treatment with the 500 mg herbal composition described above, his Symptom Checklist score had decreased to a value of 17.

This participant was suffering from incontinence and the inability to empty his bladder. This participant reported that his urologist had tried many treatments, but none of them had provided any relief. After being treated with the herbal compositions according to this invention for about two months, this individual reported that he felt much healthier. At the end of the two-month treatment period, he was able to completely empty his bladder and the pressure in his bladder had greatly lessened. A urologist who checked this individual's physiological condition after the two-month treatment period confirmed that this individual's bladder was being emptied upon urination.

Example 10

A female, age 77, weight 120 lbs, had a beginning Symptom Checklist score of 18. After about two months of treatment with the 500 mg herbal composition described above, her Symptom Checklist score had decreased to a value of 9.

Before treatment with the herbal composition, the participant was experiencing incomplete emptying, frequent urination, intermittency in urination, and difficulty in postponing urination. The participant had also been experiencing bladder pain for about eight years. After being treated with the herbal compositions according to this invention for about two months, this individual reported decreased bladder pain. At the end of the two-month treatment period, all the participant's reported symptoms were improved.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A preparation for treatment of urogenital/urological disorders comprising at least part of a plant, wherein the part of the plant is pulverized and wherein the plant is Wyethia amplexicaulis.

2. A preparation as recited in claim 1, wherein the preparation includes the at least part of the plant in an amount of 500 milligrams.

3. A preparation as recited in claim 1, wherein the preparation is encapsulated.

4. A preparation as recited in claim 1, wherein the preparation is packaged for mixing with a liquid to be ingested as an herbal tea.

5. A method for treating a urogenital/urological disorders comprising administering a therapeutically effective amount of the preparation of claim 1.

6. A method as recited in claim 5, wherein the preparation is administered in capsule.

7. A method as recited in claim 5, wherein the preparation is administered in a capsule and the therapeutically effective amount of the preparation is 500 milligrams on a daily basis.

8. A method as recited in claim 5, wherein the preparation is administered in a liquid preparation.

9. A method for preparing the preparation of claim 1 for treatment of urogenital/urological disorders comprising:
    cleaning the plant,
    pulverizing at least part of the plant, and
    packaging the pulverized plant for administration of a therapeutically effective
    amount of the pulverized plant.

10. A method as recited in claim 9, wherein the pulverized plant is packaged in a capsule.

11. A method as recited in claim 9, wherein the pulverized plant is packaged in a capsule and the therapeutically effective amount of the pulverized plant is 500 milligrams on a daily basis.

12. A method as recited in claim 9, wherein the pulverized plant is packaged for mixing with a liquid.

13. A method as recited in claim 9, further comprising the step of drying the plant.

* * * * *